United States Patent [19]

Engelhorn et al.

[11] Patent Number: 4,745,183

[45] Date of Patent: May 17, 1988

[54] USE OF HYDROXYLAPATITE FOR THE ANALYSIS AND PREPARATION OF PURIFIED MONOCLONAL ANTIBODIES

[75] Inventors: Sheldon C. Engelhorn, San Pablo; Hector Juarez-Salinas, Larkspur; Gary S. Ott, Livermore, all of Calif.

[73] Assignee: Bio-Rad Laboratories, Inc., Richmond, Calif.

[21] Appl. No.: 677,145

[22] Filed: Dec. 3, 1984

Related U.S. Application Data

[63] Continuation-in-part of Ser. No. 582,089, Feb. 21, 1984, abandoned.

[51] Int. Cl.$^4$ .................... A61K 39/395; C07K 3/00; G01N 33/577
[52] U.S. Cl. ................. 530/387; 210/198.2; 210/656; 436/547; 436/548; 436/824; 530/415; 530/416; 530/808
[58] Field of Search ..................... 210/635, 656, 198.2; 424/85-87; 435/7, 68, 172.2, 240, 241, 948, 431, 803; 436/548, 824, 547; 530/387, 388, 808, 810, 415, 416

[56] References Cited

U.S. PATENT DOCUMENTS 4,469,630  12/1984  Flashner ............................. 436/548

OTHER PUBLICATIONS

Regnier, F. E., Science, vol. 222(4621), pp. 245–252, 1983.
LKB2204-HA Catalogue, 5/80.
Bio–Rad Catalogue, Chemical Division, Jan. 1984, pp. 104–106, (Chromatography).
Chemical Abstracts, 101:70595a, (1984).

Primary Examiner—Sidney Marantz
Attorney, Agent, or Firm—Townsend and Townsend

[57] ABSTRACT

A novel method is disclosed for the purification of monoclonal antibodies from antibodies of the same isotype but different light chain composition which are frequently present in the fluids in which such antibodies are generated. According to the method, the mixture is placed in a hydroxylapatite chromatography column and eluted with a buffer solution in a concentration gradient elution. With the appropriate optimization of system parameters, a separation of antibodies effective for both analytical and preparative purposes is obtained.

8 Claims, No Drawings

USE OF HYDROXYLAPATITE FOR THE ANALYSIS AND PREPARATION OF PURIFIED MONOCLONAL ANTIBODIES

CROSS REFERENCE TO RELATED APPLICATION

This application is a continuation-in-part of Applicant's copending application, Ser. No. 582,089, filed Feb. 21, 1984, now abandoned.

BACKGROUND OF THE INVENTION

The present invention relates to the purification of immunoglobulins. In particular, the invention relates to the purification of monoclonal antibodies by high performance liquid chromatography on the basis of variations in light chain structure.

Purified preparations of monoclonal antibodies are often difficult to obtain since fluids from which they are purified are frequently contaminated with antibodies of unknown specificity. Although conventional chromatographic procedures often yield purified immunoglobulin fractions as analyzed by SDS-PAGE, the presence of contaminating antibodies of the same class cannot be ruled out. Therefore, time-consuming techniques are often necessary to properly analyze purified immunoglobulin fractions. An ideal procedure for the analysis of monoclonal antibody preparations should be fast, reproducible and easy to perform. Further, it should be useful for both analytical and preparative purposes.

SUMMARY OF THE INVENTION

It has now been discovered that monoclonal antibodies can be separated from inactive immunoglobulins (i.e., immunoglobulins having specificities different from the desired monoclonals) of the same heavy chain isotypes but different light chain composition by the use of hydroxylapatite chromatography. This simple and highly effective technique is useful and effective on both analytical and preparative scales due to capacity and reproducibility.

DETAILED DESCRIPTION OF THE INVENTION

The present invention is applicable to mono-clonal antibodies generated either in vitro or in vivo. The separation is generally carried out by elution through a liquid chromatography column, preferably a high performance column, using conventional techniques.

The elution is done using a gradient technique under preferably constant pH. The pH itself is not critical to the utility of the separation, but preferably lies within the range of about 5.0 to about 9.0 most preferably from about 6.0 to about 8.0. The gradient is provided by increasing the buffer concentration throughout the course of the separation. A variety of buffer materials well known in the art of high performance chromatography may be used, and the concentration and rate of increase will vary with each. For sodium phosphate buffer systems, the separation is preferably run by starting with a concentration of from zero to about 0.01 M and increasing to a final concentration of from about 0.12 M to about 0.3 M, preferably in continuous or stepwise fashion. The flow rate is appropriately adjusted to result in the optimum degree of separation, and the inlet pressure to the column is chosen accordingly to achieve the desired flow rate. In general, all such adjustments and optimizations are within the routine skill of an experienced laboratory technician.

Detection of the peaks eluting from the column for purposes of determining the effectiveness of the separation is also achieved by conventional techniques, including UV absorbance, conductivity and fluorescence detection.

The invention is applicable to immunoglobulins in general, including the various subclasses of IgG, IgM, IgE, IgA, and IgD. In the preferred practice of the invention, the antibodies are of one of the IgG types.

The following example is offered for purposes of illustration and is not intended to limit or define the invention in any manner.

EXAMPLE

In this example, the following abbreviations are used:
HPHT: High Performance Hydroxylapatite
HPLC: High Performance Liquid Chromatography
DEAE: Diethylaminoethyl Cellulose
SDS-PAGE: Sodium dodecylsulfate polyacrylamide gel electrophoresis
ELISA: Enzyme-linked Immunosorbance Assay.

A monoclonal antibody (10F7) directed against glycophorin A, a human erythrocyte membrane that carries the M and N blood group determinants, was obtained from hybridoma derived from SP2/0 myeloma cells and spleen cells from Biozzi mice immunized with a mixture of human erythrocytes from homozygous blood group M and N. Purification of the immunoglobulin fraction from mouse ascites fluid was achieved by chromatography on Protein A-Agarose. SDS-PAGE of this fraction yielded bands corresponding to the heavy and light immunoglobulin chains. Analysis of this preparation by HPHT was performed in an HPLC Gradient Processor System equipped with a variable length UV monitor, Model 1305, a conductivity monitor, a 100 microliter injection loop, and a 100×7.8 mm Bio-Gel HPHT column with a 50×4 mm Bio-Gel HPHT guard column (Bio-Rad Laboratories, Richmond, CA). After sample injection, a linear gradient from 10 to 300 mM in sodium phosphate buffer, pH 6.8, was used for sample elution. UV absorbance was monitored at 280 nm. Total chromatography time was 30 minutes. Three well-resolved peaks eluting at 62, 80, and 90 mM $NaH_2PO_4$ buffer concentrations were observed. Peaks I, II, and III were all immunoglobulins of the $IgG_1$ isotype. When the activity of each peak was determined by an ELISA-based method using purified glycophorin A as the antigen, over 90% of the initial activity present in the ascites fluid was recovered in Peak III, with a trace of activity in Peak II. The material in Peak I was inactive.

Each peak was then chromatographed by electrophoresis on a reducing SDS-PAGE gel which resulted in separation of all chains. In addition to the heavy chain bands, the Peak I material gave a single slow-moving band, the Peak III material a single fast-moving band, and the Peak II material gave both. These observations, together with the activity tests, indicate that two different types of light chain were present, the Peak I antibodies having two of one type, the Peak III antibodies having two of the other, and the Peak II antibodies having one of each.

It will be readily apparent to those skilled in the art that modifications and variations of the above will still fall within the general concept of the invention. For this reason, the invention is not intended to be limited to the particular features described above, but rather by the claims which follow.

What is claimed is:

1. A method for the separation of an antibody of selected light chain composition from a mixture containing antibodies of the same isotype but different light chain composition, said method comprising:
   (a) impregnating a hydroxylapatite chromatography column with said mixture;
   (b) passing through said column an elution buffer of increasing concentration to cause said mixture to elute therefrom in substantially separate peaks according to light chain composition; and
   (c) recovering from the eluate of step (b) a fraction containing the peak corresponding to said antibody of selected light chain composition.

2. A method according to claim 1 in which said isotype is an IgG isotype.

3. A method according to claim 1 in which the pH of said buffer is constant throughout step (b), and is within the range of from about 5.0 to about 9.0.

4. A method according to claim 1 in which the pH of said buffer is constant throughout step (b), and is within the range of from about 6.0 to about 8.0.

5. A method according to claim 1 in which the increase of step (b) is continuous.

6. A method according to claim 1 in which said elution buffer is aqueous sodium phosphate.

7. A method according to claim 6 in which the increasing concentration of step (b) ranges from an initial concentration of zero to about 0.01 M to a final concentration of from about 0.12 M to about 0.3 M.

8. A method for purifying monoclonal antibodies from fluid mixtures containing antibodies of the same isotype but different light chain composition, said method comprising:
   (a) impregnating a hydroxylapatite chromatography column with said mixture;
   (b) passing through said column an aqueous sodium phosphate buffer solution at a pH ranging from about 6.0 to about 8.0, the concentration of said solution continuously increasing in linear manner from an initial level ranging from about 0.12 M to about 0.3 M, to cause said mixture to elute therefrom in substantially separate peaks according to light chain composition; and
   (c) recovering from the eluate of step (b) a fraction containing the peak corresponding to said monoclonal antibodies.

* * * * *